Figure 2:
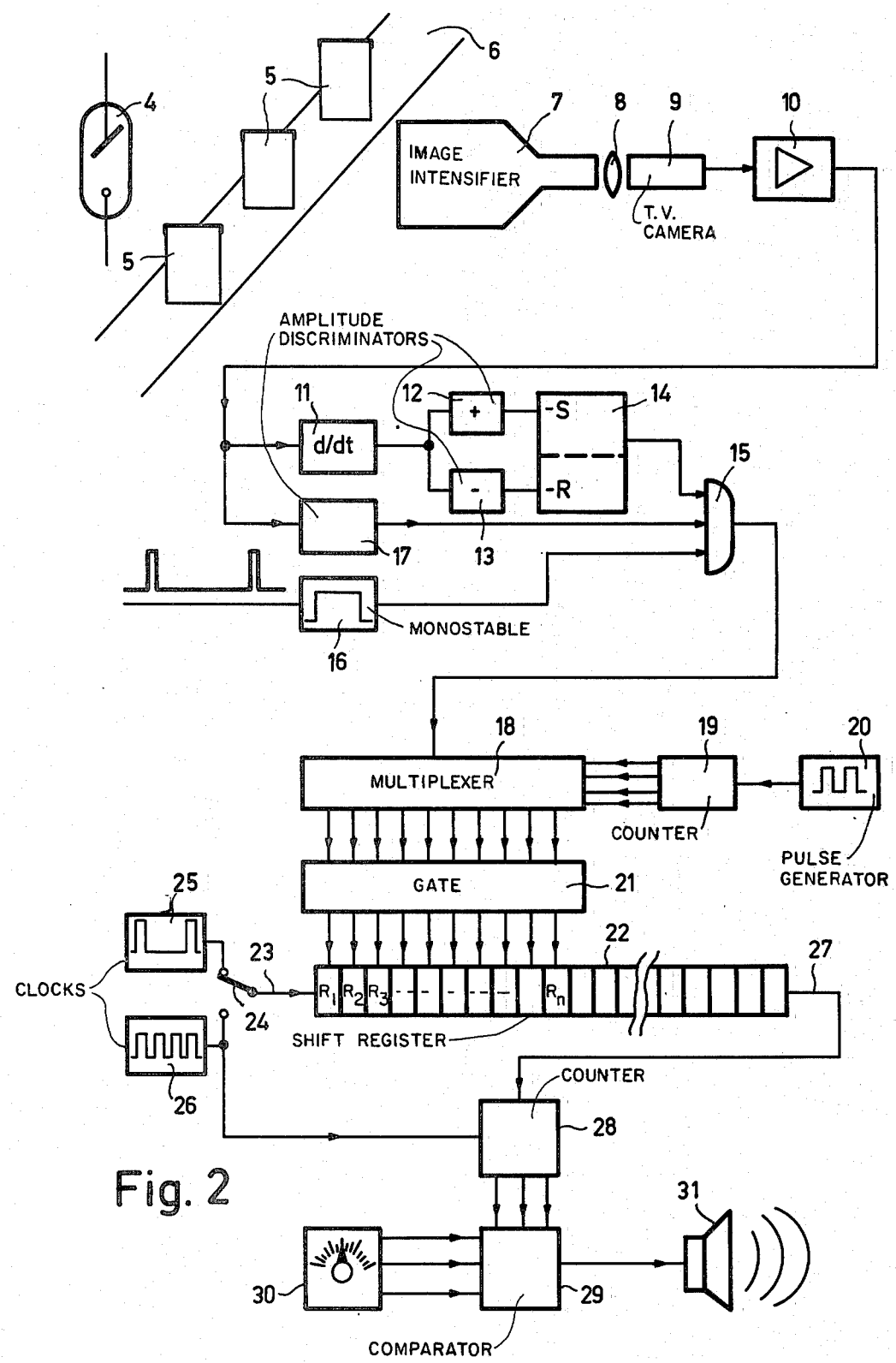

United States Patent [19]

Burrig

[11] 4,163,991
[45] Aug. 7, 1979

[54] ARRANGEMENT FOR EXAMINING OBJECTS

[75] Inventor: Thomas Burrig, Hamburg, Fed. Rep. of Germany

[73] Assignee: U.S. Philips Corporation, New York, N.Y.

[21] Appl. No.: 903,546

[22] Filed: May 8, 1978

[30] Foreign Application Priority Data

May 10, 1977 [DE] Fed. Rep. of Germany ....... 2720865

[51] Int. Cl.² .......................................... H04N 7/18
[52] U.S. Cl. .................................. 358/111; 358/106; 250/563
[58] Field of Search ................ 358/110, 111, 106, 93, 358/107, 113; 250/562, 563, 572; 356/237

[56] References Cited

U.S. PATENT DOCUMENTS

| 4,031,545 | 6/1977 | Stein et al. | 358/111 |
| 4,091,416 | 5/1978 | Riethmuller | 358/111 |

*Primary Examiner*—Robert L. Griffin
*Assistant Examiner*—Edward L. Coles
*Attorney, Agent, or Firm*—Thomas A. Briody; Edward J. Connors, Jr.; Jack E. Haken

[57] ABSTRACT

An arrangement for detecting foreign objects in products. The products are X-rayed to produce a quantized raster scanned signal. The samples thus obtained for each line are combined with the bit samples of the next line, shifted by at least one position, and the output signal is applied to an evaluation arrangement which supplies an alarm signal when a foreign object is present.

5 Claims, 5 Drawing Figures

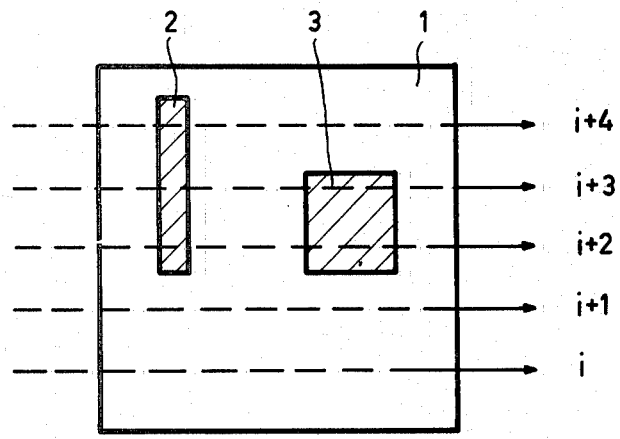
Fig. 1a
Fig. 1b
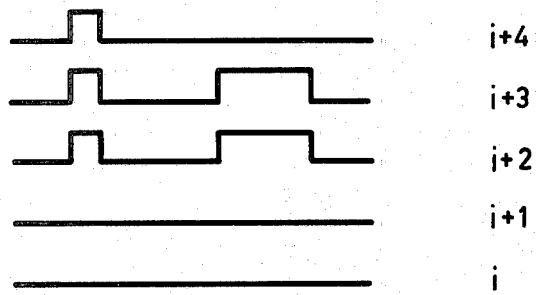
Fig. 1c

ARRANGEMENT FOR EXAMINING OBJECTS

The invention relates to an arrangement for examining objects for regions whose emission, absorption or reflection deviates from that of the surrounding regions, comprising a scanning device which scans the object line-by-line and supplies a scanning signal depending on the emission, absorption or reflection, and means for generating an identification signal when a region is scanned whose emission absorption or reflection considerably deviates from that of the surrounding regions.

The principle of such an arrangement is disclosed in German published Patent Application No. 15 74 111; the objects to be examined, for example cakes of soap, are passed in front of a source of X-ray radiation and the radiation pattern thus generated is converted into a visible image by means of an image intensifier and scanned line-by-line by means of a television camera. Depending on the amplitude of the video signal produced by the television camera a gate is opened which connects the video signal to a differentiating circuit and an amplitude discriminator. When a video signal is within a certain amplitude range, the gate is opened and when the differentiated video signal exceeds a pre-adjustable threshold value the amplitude discriminator generates a signal which results in a sorting-out process.

The output signal depends on the size of the scanned foreign object, that is to say a small foreign object, which can just be defined by means of the television camera, in the examined object results in a sorting-out process. However, this reaction to very small foreign objects is undesirable in many examinations. This can, in principle, be avoided by increasing the diameter of the scanning electron beam so that the resolution is reduced, but then it is difficult to detect long, thin foreign objects, particularly when they are in a vertical position or at an angle relative to the line direction. A further drawback of the known arrangement is that brief spurious signal having a large slope may cause a sorting-out process.

It is an object of the invention to provide an arrangement in which portions of a foreign object which are perpendicular to the line direction are taken into account and which is considerably less sensitive to spurious signals.

In accordance with the invention this is accomplished by an arrangement comprising:

a coding device which adds binary signals to each line n(n>1), the logic level of these signals assuming a first value when the identification signal is produced and a second value when the identification signal is not produced, a store into which the bit sample thus obtained is entered, a gate arrangement which functions as an OR-gate for the logic level associated with the identification signal and which combines the bit samples of at least two lines which are shifted at least one binary position relative to one another, and an evaluation arrangement which processes the bit sample resulting from the combination and which activates a signalling or a sorting-out arrangement at the occurrence of several consecutive logic levels associated with the identification signal.

Figure 3:
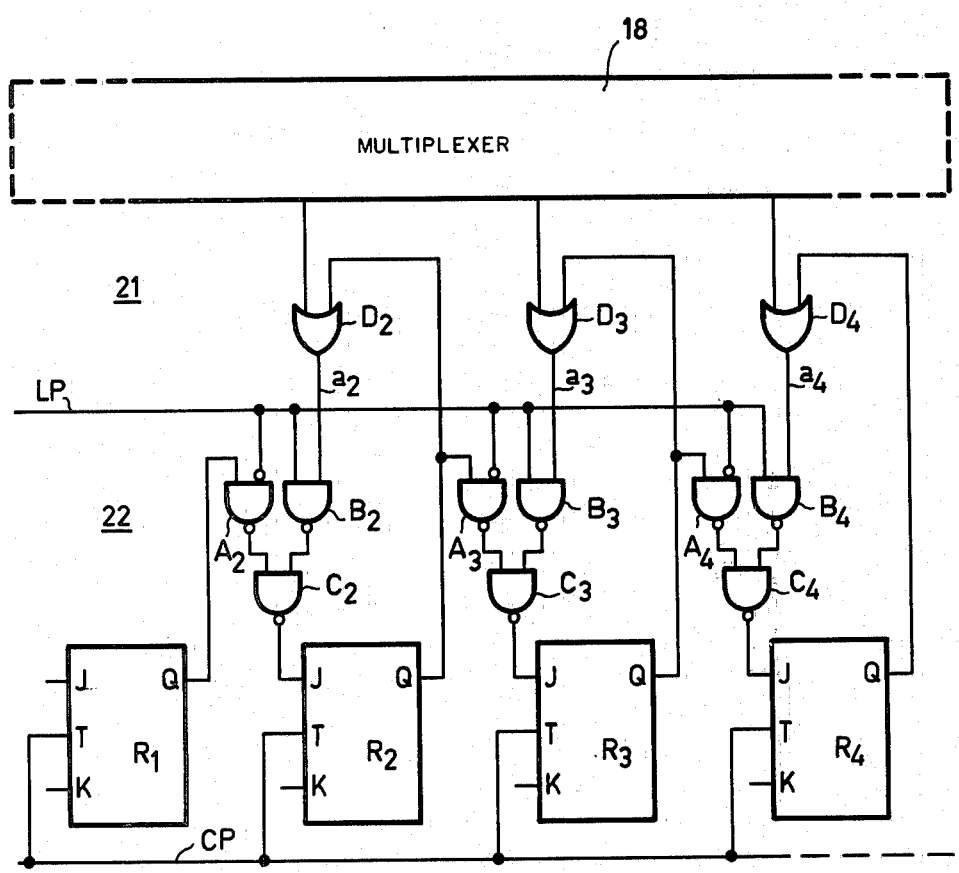

The operation of the invention will be further explained with reference to the Figures in which FIG. 1a shows a portion of an object which portion is scanned line-by-line, FIG. 1b shows the associated variation versus the time of an identification signal, FIG. 1c shows the bit sample obtained therefrom and shifted each time over one binary position, FIG. 2 is a block diagram of an arrangement according to the invention, and FIG. 3 shows a detailed circuit diagram of a gate arrangement and a parallel-in, series-out shift register.

In FIG. 1a reference numeral 1 denotes the object to be examined or part thereof and references 2 and 3, respectively, denote elongated and square foreign object present in the object. The foreign object it is assumed to have a different absorption, emission or reflection for the radiation used. Object 1 is scanned by a scanning device in the horizontal direction along the lines i, i+1...i+4. The variation versus the time of the identification signal thus obtained is shown in FIG. 1b for the individual lines. A bit sample which is stored and is shifted one binary position relative to the bit sample generated from the preceding line (FIG. 1c) is obtained from these identification signals by means of a coding device. The binary signal shown at the bottom of FIG. 1c is then obtained by means of an OR-gate. For the foreign objects 2 and 3 this bit sample comprises three "1" bits associated with an identification signal or a foreign object. The size of a foreign object which is perpendicular to the scanning lines is detected and the bit sample depends on the size of the foreign object. Furthermore, each fairly large foreign object is characterized by several consecutive binary positions, each comprising a logic level "1". An evaluation device which effects a signalling or sortingout process only at the occurrence of several consecutive logic "1" levels consequently does not react to brief interferences which each time produce only one binary position in the bit sample.

In principle it is possible to store the whole bit sample associated with the scanned field, to shift the bit samples associated with a line one binary position and to perform the OR-combination. If, however, the bit sample comprises considerably more binary positions per scanning line than are shown schematically in FIG. 1c and if considerably more scanning lines are used for scanning the field to be examined, storing and combining apparatus becomes very expensive. In accordance with a further embodiment of the invention the store is a shift register, it being possible to enter the bit sample of a line in parallel into this shift register. The contents of the shift register are shifted one storage position at the end of a line and are serially applied to the evaluation device at the end of a field. Such a shift register requires only n+z register sections, n representing the plurality of binary positions per line and z the plurality of lines necessary for scanning the field.

The invention will now be explained in greater detail with reference to the embodiment shown in FIG. 2.

Rays emitted by an X-ray source 4 are passed through the objects to be examined 5, for example cylindrical jars which may contain foreign objects, for example in the form of glass splinters. The jars are transported by means of a conveyor belt 6 which travels in a direction perpendicular to the direction of the radiation. The radiation pattern produced during X-ray examination of the jars 5 is depicted on an input screen of an image intensifier 7, a reduced visible image being produced on an output screen, which image is projected by means of an optical device 8, on the target plate of a television camera 9. The video signal produced thereby is amplified by a video amplifier 10.

An identification signal is generated when a region whose absorption considerably deviates from that of the regions surrounding it (foreign object) is scanned. If the object to be examined has a uniform thickness and, consequently, a uniform absorption, such an identification signal could be generated by means of a threshold-value switch which reacts for the time the video signal is above or below a threshold value corresponding to the normal absorption value. This is not possible when an object is examined which does not have a uniform thickness. In that case the value of the time derivative of the scanning signal must be used as an indication for the presence of a foreign object. To this end a differentiating circuit 11 is provided whose input is connected to the output of the video amplifier 10 and whose output signal is applied to the inputs of two amplitude discriminators 12 and 13, one of which (12) becomes operative when the output signals of a positive polarity exceed a predetermined (positive) threshold value. The other discriminator (13) becomes operative when the output signal exceeds a predetermined (negative) threshold value.

When scanning a foreign object which has a different absorption, two signal peaks of opposite polarity are produced at the output of the differentiating circuit 11, one of the peaks being produced when the leading edge is scanned and the other when the trailing edge is scanned. Consequently, the output pulses of the amplitude discriminators 12 and 13 correspond to the beginning and the end of the foreign object within the scanned line. These output pulses are applied to the setting input (S) and resetting input (R), respectively, of a flipflop 14, the state of which at any instant therefore depends on whether a foreign object is being scanned. The output of the flipflop is connected to an input of an AND-gate 15.

An other input of this AND-gate 15 is connected to the output of a monostable trigger circuit 16, to whose input line-frequency pulses are applied and which supplies a signal having a pulse duration corresponding to the period of time required for scanning a line in the television picture. This causes all spurious signals which might occur during, for example, line flyback, to be suppressed.

Finally, a third input of the AND-gate 15 is connected to the output of an amplitude discriminator 17 which produces an output when the instantaneous value of the video signal is within a given amplitude range. This amplitude range corresonds to the amplitude range to be expected when scanning a normal object. In the relevant case the amplitude range of the discriminator 17 has been chosen so that the discriminator does not react when the side of the jars 5 is scanned, a very strong absorption by the glass then occurring, but that a reaction occurs only when less absorption occurs (i.e. when the food in the glass is scanned). Thus the amplitude discriminator 17 selects the food which must be examined for foreign objects. In the case of more complicated objects several amplitude discriminators for different amplitude ranges may be provided.

At the beginning of the scanning of a foreign object the output signal of the AND-gate 15 consequently assumes a first logic level (for example "1"), retains this level until the end of the foreign object is scanned whereafter it changes to the other logic level ("0"). This output signal will be called the identification signal. The identification signal is applied to the input of a multiplexer 18 and is successively connected to one of the n-outputs. Clock inputs for the multiplexer 18 are supplied by a counter 19, which counts the output of a pulse generator 20 which is synchronized with the horizontal scanning frequency so that n pulses are generated during the scanning of a line. In combination the counter 19, the pulse generator 20 and the multiplexer 18 together constitute a coding device (18-20). The output of the multiplexer 18 is a bit sample which characterized the absorption ratios along one line, the line being divided into n portions. An output bit is associated with each portion in the same sequence as the sequence of the periods in the scanning signal.

The multiplexer 18 and the counter 19 can be dispensed with if the multiplexer is replaced by a shift register, having n register sections and an input for receiving the identification signals, which is clocked by the pulse generator 20. At the end of a line the shift register contains the bit samples which are derived in parallel from the output of the register sections.

The n outputs of the multiplexer 18 are connected via an OR-gate arrangement 21 to a corresponding number of parallel inputs of a shift register 22 which operates as a store, so that the bit samples which are successively produced in time at the multiplexer outputs are entered into the first n sections of the shift register 22. Successive pulses at a clock input 23 shift the content of the shift register 22 one section to the right. The clock input 23 of the shift register 22 can optionally be connected to a first clock 25 or a second clock 26 by means of a change-over switch 24. The clock 25 is synchronized to the horizontal scanning so that a shift pulse is generated during each line flyback so that after scanning a line the contents of the register sections are shifted one section to the right.

For each of the n outputs of multiplexer 18 the OR-gate arrangement 21 may comprise (FIG. 3) an OR-gate D having two inputs, one of which is connected to an output of the multiplexer 18 and the other input to the output of a register section R. The output of the relevant OR-gate D is connected to an input of this same register section R. FIG. 3 shows the register sections $R_1 \ldots R_4$ in the form of JK flipflops having trigger inputs T which are connected to a clock bus CP and Q-outputs connected to the J-input of the next register flipflop via a circuit comprising three NAND-gates A, B, C. The outputs of the gates A and B respectively, are connected to the J-input via the gates C and a first input is connected to the Q-output of the preceding register section R or to a (parallel) data input a from gate D. The second inputs are connected to a transfer bus LP. The transfer bus input of the gates A is an inverting input. Depending on the logic level at the transfer bus LP either the output signal of the gate D or the output signal of the preceding register section R is stored in the next register section as a clock pulse appears at the lead CP. This causes the bit sample of the first line which has been shifted one position to the right, to be ored with the bit sample of the second line so that the content of the storage sections R is changed when the bit sample of the second line is "1" in the relevant position, (that is to say a logic level associated with he identification signal of a foreign object) and a "0" has been stored in the relevant register section. Thus the number of sections storing the logic level "1" can only be increased.

The bit sample processed in the described manner by means of the OR-gate arrangement 21 is again shifted one binary position to the right at the end of the second line and is combined with the bit sample for the first line in the manner described. This can be repeated until the bit samples of all lines of a field have been combined with the bit sample of the preceding lines. In this case the shift register 22 must comprise z (z=number of lines of a field) register sections R are necessary per se for storing the binary samples of a line.

The change-over switch 24 of FIG. 2 is changed-over at the end of each field so that the clock input 23 is connected to the output of clock 26 which supplies pulses of a considerably higher frequency, which causes the combined bit sample to appear at a high rate at a series output 27 of the shift register 22. The sequentially appearing bit sample is processed by a subsequent evaluation circuit so that a signal device is actuated or a sorting-out process effected when this bit sample contains a given predetermined number of successive "1" bits. To this end the evaluation arrangement may, for example, comprise a shift register having a number of register sections corresponding to the predetermined number, in which the bit sample at the output 27 is sequentially entered. The output of this shift register are interconnected in parallel via an AND-gate so that an actuating signal is only obtained when all register sections simultaneously contain "1"'s. It would then, however, be difficult to change the number of "1" signals required for an actuation procedure.

Alternately a counter 28 having a clock input connected to the pulse generator 26 and a resetting input connected to the series output 27 of the shift register 22 may be used. Each time a "1" appears at the output 27 a counting operation starts (or if an "1" was already present immediately preceding it) a counting operation is continued. Resetting occurs as soon as a "0" appears at the output 27. The counter position attained in this manner in counter 28 is compared, in a comparator 29 to a value which can be adjusted by the user at an adjusting element 30. If this value is attained or exceeded the comparator 29 supplies a signal to a signalling device 31 or a sorting-procedure is started in a manner not further shown.

What is claimed is:

1. A device for examining objects for regions whose emission, absorption or reflection deviates from that of the surrounding regions, comprising:
    scanning means which scan the object, line-by-line, and supply a scanning signal depending on the emission, absorption or reflection;
    means for generating a binary identification signal when a region whose emission, absorption or reflection considerably deviates from that of the surrounding regions is scanned;
    coding means which produce binary sample signals corresponding to samples of said identification signal at a plurality of discrete positions on said scan lines, the logic level of said sample signals assuming a first value when the identification signal is present and a second value when the identification signal is not present;
    a store connected to receive the sample signals;
    a gate means which produce a relative shift of at least one discrete position between sample signals associated with successive lines and which combine said shifted sample signals by ORing logic levels of said first value; and
    evaluation means which process the result of said combination and which activate a signal upon the occurrence therein of several consecutive logic levels associated with the identification signal.

2. A device as claimed in claim 1, wherein the store comprises:
    a shift register connected to receive the sample signal of a line in parallel; and the gate means comprise
    means for shifting the contents of said shift register one storage position at the end of each line; and
    means for applying the contents of said shift register to said evaluation means at the end of a field.

3. A device as claimed in claim 2, wherein the coding means comprise a multiplexer having a number of outputs corresponding to the number of discrete positions per line, connected to receive an input line which changes synchronously with the identification signal and controlled by a counter which is connected to count pulses having a period of 1/n of the duration of a scanning line.

4. A device as claimed in claim 1, 2 or 3, wherein the evaluation means comprise a counter having a resetting input connected to a serial output of the store, an input connected to receive a pulse series having a pulse rate corresponding to the serial output bit rate and an output connected to comparision means which compare the counter position with a predetermined value and thereby control the signal.

5. A device as claimed in claims 1, 2 or 3, further comprising differentiating means which generate the identification signal from the scanning signal threshold value means which receive the output of the differentiating means and control the state of a bistable trigger circuit when a positive or negative threshold value is exceeded thereby.

* * * * *